US009637724B2

(12) United States Patent
Gagnon (10) Patent No.: US 9,637,724 B2
(45) Date of Patent: May 2, 2017

(54) SELECTIVE BINDING OF BIOLOGICAL TARGETS TO SOLID PHASE UREIDES

(71) Applicant: AGENCY FOR SCIENCE, TECHNOLOGY AND RESEARCH, Connexis (SG)

(72) Inventor: Peter Gagnon, Centros (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 0 days.

(21) Appl. No.: 14/555,288

(22) Filed: Nov. 26, 2014

(65) Prior Publication Data

US 2015/0184132 A1 Jul. 2, 2015

Related U.S. Application Data

(63) Continuation of application No. PCT/SG2013/000218, filed on May 30, 2013.

(60) Provisional application No. 61/653,740, filed on May 31, 2012, provisional application No. 61/653,729, filed on May 31, 2012, provisional application No. 61/774,441, filed on Mar. 7, 2013.

(51) Int. Cl.

| A61K 39/00 | (2006.01) |
|---|---|
| A01N 37/18 | (2006.01) |
| A01N 43/16 | (2006.01) |
| A01N 43/78 | (2006.01) |
| A01N 43/90 | (2006.01) |
| C12N 7/00 | (2006.01) |
| C07H 1/08 | (2006.01) |
| C07K 1/36 | (2006.01) |
| C07K 14/77 | (2006.01) |
| C07K 16/00 | (2006.01) |
| C12N 5/071 | (2010.01) |
| B01D 15/26 | (2006.01) |
| B01D 15/38 | (2006.01) |
| B01J 20/286 | (2006.01) |
| B01J 20/32 | (2006.01) |
| C07K 1/22 | (2006.01) |

(52) U.S. Cl.
CPC ............. *C12N 7/00* (2013.01); *B01D 15/265* (2013.01); *B01D 15/3804* (2013.01); *B01J 20/286* (2013.01); *B01J 20/3251* (2013.01); *C07H 1/08* (2013.01); *C07K 1/22* (2013.01); *C07K 1/36* (2013.01); *C07K 14/77* (2013.01); *C07K 16/00* (2013.01); *C12N 5/0602* (2013.01); *C12N 2770/24151* (2013.01); *C12N 2795/00051* (2013.01)

(58) Field of Classification Search
CPC ........ C12N 7/00; B01D 15/3804; C07H 1/08; C07K 14/77; C07K 16/00
See application file for complete search history.

(56) References Cited

U.S. PATENT DOCUMENTS

| 6,554,886 B2 | 4/2003 | Yoshikawa et al. |
|---|---|---|
| 2003/0231981 A1* | 12/2003 | Johnson .............. A61M 1/3679 422/44 |
| 2009/0247735 A1* | 10/2009 | Gagnon ................ C07K 1/165 530/413 |

FOREIGN PATENT DOCUMENTS

| CN | 102010372 A | * 4/2011 |
|---|---|---|
| JP | 2006-508703 | 3/2006 |
| SG | 195306 | 12/2013 |
| WO | WO 03/090924 | 11/2003 |
| WO | 2012169970 A1 | 12/2012 |
| WO | WO2012169970 | * 12/2012 |

OTHER PUBLICATIONS

Kim et al., "Impermeant antitumor sulfonylurea conjugates that inhibit plasma membrane NADH oxidase and growth of HeLa cells i culture. Identification of binding proteins from sera of cancer patients", 1997, Biochimica et Biophysica Acta:171-181.*
Kim et al., The Journal of Biological Chemistry, 2007, 282(32):23457-23464.*
Kim et al., "Impermeant antitumor sulfonylurea conjugates that inhibit plasma membrane NADH oxidase and growth of HeLa cells in culture. Identification of binding proteins from sera of cancer patients," Biochimica et Biophysica Acta 1324 (1997) 171-181.
Gan et al., "Characterization and removal of aggregates formed by nonspecific interaction of IgM monoclonal antibodies with chromatin catabolites during cell culture production," J. Chromatogr. A 1291 (2013) 33-40.
Vagenede et al., "Amide-Mediated Hydrogen Bonding at Organic Crystal/Water Interfaces Enables Selective Endotoxin Binding with Picomolar Affinity," American Chemical Society (2013) 4472-4478.
Tu et al., "Silica gel modified with 1-(2-aminoethyl)-3-phenylurea for selective solid-phase extraction and preconcentration of Sc(III) from environmental samples," Talanta 80 (2010) 1205-1209.
Kotoni et al., "Design and evaluation of hydrolytically stable bidentate urea-type stationary phases for hydrophilic interaction chromatography," Journal of Chromatography A, 1232 (2012) 196-211.
Bicker et al., "Retention and selectivity effects caused by bonding of a polar urea-type ligand to silica: A study on mixed-mode retention mechanisms and the pivotal role of solute—silanol interactions in the hydrophilic interaction chromatography elution mode," Journal of Chromatography A, 1218 (2011) 882-895.
European Search Report issued Mar. 1, 2016 in corresponding European Patent Application No. 13798068.6 (8 pages).
Singapore Written Opinion issued Apr. 12, 2016 in corresponding Singapore Patent Application No. 11201407800S (7 pages).
Japanese Office Action dated Dec. 13, 2016 for Appln. No. 2015-514967.

* cited by examiner

*Primary Examiner* — Janet L Andres
*Assistant Examiner* — Barry A Chestnut
(74) *Attorney, Agent, or Firm* — Pillsbury Winthrop Shaw Pittman, LLP (57) ABSTRACT

A method of selectively separating a biological target from a sample including the biological target material or suspected of including the biological target includes the steps of (i) providing a solid including ureide moieties at its surface, (ii) contacting the sample with the solid, whereby a substantial fraction of the biological target in the sample binds to the ureide moieties, and (iii) separating the solid from the sample.

49 Claims, 3 Drawing Sheets

SELECTIVE BINDING OF BIOLOGICAL TARGETS TO SOLID PHASE UREIDES

CROSS-REFERENCE TO RELATED APPLICATIONS

This application is a continuation of PCT/SG2013/000218 filed May 30, 2013, which claims the priority of U.S. Provisional Application No. 61/653,740, filed May 31, 2012 and U.S. Provisional Application No. 61/653,729 filed May 31, 2012, and U.S. Provisional Application No. 61/774,441 filed Mar. 7, 2013, the disclosures of which are incorporated herein by reference in their entireties.

FIELD

Embodiments disclosed herein relate to methods for the use of solid surfaces bearing ureides to selectively bind biological targets existing independently or in assemblages. Such biological target may vary widely in size and, in particular embodiments, their size may include from about 20 microns or more to millions of Daltons. Such biological targets particularly include cells, substructures of cells, viruses, and/or aggregates, where the purpose of the methods is to remove them from a local environment, potentially to purify them for subsequent use. Methods disclosed herein may be further integrated with other fractionation steps to achieve a higher degree of purification of either the large biological target, or further purification of a different desired component of a sample from which the large biological targets have been removed.

BACKGROUND

Precipitation methods can be classified into two groups: precipitation and coprecipitation, based on the functional mechanisms involved. Classical precipitation methods usually employ large amounts of additives that alter the characteristics of the solvent in a way that renders the species to be precipitated insoluble. The additive itself may remain soluble and is mostly removed when the supernatant is separated from the precipitate. The precipitate is then resuspended in a fluid lacking the agent that was used to mediate precipitation. Traces of the agents can be easily removed since they do not form persistent associations with the product being precipitated. Examples include precipitation with salts such as ammonium sulfate, sodium citrate, and potassium phosphate, among others; organic polymers such as polyethylene glycol, polypropylene glycol, dextran, and polyvinylpyrrolidone, among others; and organic solvents such as acetone, chloroform, and alcohols, among others.

Co-precipitation methods typically work by binding to a species to be precipitated and reducing its solubility to a point where it precipitates spontaneously. The technique can be used to selectively precipitate a protein or virus of research or commercial interest. Equally, the technique can be used to selectively precipitate one or more contaminant species from a preparation containing proteins or DNA plasmids of interest. Contaminants that are important to remove from protein and DNA plasmid preparations particularly include viruses and endotoxins. Co-precipitation is generally advantageous over classical precipitation in the sense that it usually uses lower amounts of the precipitating agent, but disadvantageous in the sense that recovery of the precipitated product employs not only its re-suspension in the absence of precipitating agent, but may impose the need for an additional processing step to displace residual precipitating agent that remains bound in trace amounts to the product of interest. This is usually done by introducing an agent that disrupts the interaction between the product and the co-precipitant. Examples of co-precipitating agents include anionic polymers, cationic polymers, and fatty acids, among others. Substances used to displace residual precipitating agent include high concentrations of neutral salts such as sodium chloride, chaotropes, and organic solvents, among others.

Both classical precipitation methods and co-precipitation methods have been used in the purification of virus. Many types of chemical surfaces have the ability to bind virus. Some include surfaces that are chemically modified to mediate interactions with viruses through positive or negative charges, or hydrophobicity, such as ion exchangers and hydrophobic interaction chromatography media. These materials have the desirable feature of binding diverse virus species and fairly low cost, but also the undesirable features of binding a great number of proteins and requiring extensive process development. Alternatively, immobilization of antibodies as bioaffinity ligands on surfaces can be specific for virus as opposed to other proteins and require only limited process development, but surfaces with immobilized antibodies typically bind only a single virus species and they are comparatively very expensive.

Ureides have exhibited activity as non-inflammatory or anti-inflammatory agents that are used widely in products for human skin care. One common example is allantoin, which is poorly soluble in aqueous solutions and saturates at a concentration of about 36 mM. Amounts above this concentration exist as crystals. Some ureides have been covalently immobilized on silica particles. Immobilization of 1-[3-(trimethoxysilyl)propyl]urea on silica has been demonstrated (Bicker et al. J. Chromatogr. A, 1218 882-895 2011), and the construct used for hydrophilic interaction chromatography of a variety of small molecule compounds. A bidentate alkoxysilane has been immobilized (Kotoni et al J. Chromatogr. A, 1232 196-211 2012) incorporating urea fragments on silica, also for hydrophilic interaction chromatography, and was found to be useful for the analysis of sugars. The use of allantoin in combination with multivalent cations for clarification of aggregates from antibody-containing cell culture supernatants has been described (J. Chromatogr. A, 1291 33-40 2013).

SUMMARY OF THE INVENTION

Embodiments disclosed herein provide methods for selectively separating biological targets from a sample, including the steps of (i) providing a solid having one or more ureide moieties at its surface; (ii) contacting the sample with the solid, whereby a substantial fraction of biological targets in the sample binds to the ureides on the surface of the solid; and (iii) separating the solid from the sample. In some embodiments, the biological targets are considered "large." The term "large," as used herein in reference to biological targets, will be understood to include individual biological targets or assemblages of biological targets with an aggregate size from about 20 microns to millions of Daltons. Exemplary biological targets include cells and cellular substructures such as organelles, inclusion bodies, endotoxins, aggregates and viruses. Solids having one or more ureides at their surfaces particularly include ureide crystals or ureides immobilized on a surface. In certain embodiments the ureide particularly includes allantoin.

In certain embodiments, the sample is the local environment and the method provides means for selectively removing biological targets from that environment. In some such embodiments the sample is air, contacted with a solid material having one or more ureides on its surface. In one particular embodiment the airborne biological target is a virus or other pathogenic agent, and the ureide is allantoin.

In certain embodiments, the sample is a liquid, contacted with a solid material having one or more ureides on its surface. In one such embodiment, the sample is water, the biological targets include pathogenic microbes or derivative substructures thereof such as endotoxins, and the ureide is allantoin at a supersaturating concentration. In another such embodiment, the sample is a protein preparation containing a desired protein such as containing a recombinant protein, and the ureide is allantoin at a supersaturating concentration. In certain such embodiments, the protein preparation may contain cells, cell debris, microbes and substructures thereof including endotoxins to be removed from the liquid. In certain such embodiments, organic multivalent ions may be combined with the ureide to enhance the removal of unwanted materials. In certain such embodiments, the sample treated with the ureide and/or organic multivalent ions may be combined with other solids comprising organic multivalent ions to further enhance the removal of unwanted materials.

In certain embodiments the biological targets may be recovered from the solid having one or more ureides at its surface by dissolving the solid, or by disrupting the interaction of the target with the ureide. In one such embodiment, the ureide is allantoin. In one such embodiment, the method provides the additional step of recovering a virus from the solid wherein the sample contains a desired virus to be purified. In another such embodiment, the method provides the additional step of recovering a cellular organelle from the solid wherein the sample contains a desired organelle to be purified.

DETAILED DESCRIPTION

It has been surprisingly discovered that a solid having one or more ureides at its surface mediates a sufficiently strong affinity for biological targets, including large biological targets, that they can be selectively extracted from a sample simply by removing the solid to which they are bound. The extracted biological targets can be subsequently discarded or recovered. Large biological targets are understood to include individual targets or assemblages of targets with an aggregate size from 20 microns to millions of Daltons (D), and particularly include cells and cellular substructures such as organelles, microbes and substructures of microbes such as endotoxins, and aggregates. Smaller biological targets particularly including proteins may exhibit less affinity for ureides on a solid surface, which facilitates their separation from the larger targets bound to the ureide.

In some embodiments, the biological target has a size in a range selected from the group consisting of (1) from about 10 nm to about 200 nm, (2) from about 200 nm to about 1 micron, (3) from about 1 micron to about 20 microns), and (4) about 20 microns or greater. One skilled in the art will appreciate that the exact size of the biological target will be a function of the nature of the target itself. Where smaller biological targets are to be purified, methods disclosed herein may be combined with other purification techniques to provide the desired degree of purification.

Without being bound by any particular theory, experimental data indicate that the affinity of allantoin may be mediated through van der Walls interactions, particularly including hydrogen bonds. Such bonds are affected by pH, conductivity, and the presence of organic modifiers to a greater extent than most covalent bonds but to a lesser extent than non-covalent interactions such as electrostatic or hydrophobic interactions. This may explain why in many cases the affinity of ureides for a particular biological target is little-affected by changes in pH and salt concentration or the presence of organic modifiers that would dramatically affect electrostatic or hydrophobic interactions. The apparent affinity of ureides for a given biological target may however be affected by changes in the inherent solubility of the target as a function of pH or salt concentration or the presence of organic modifiers.

Given that the binding occurs at the ureide surface of a solid, it is apparent that the higher the total surface area of the ureide surface, the greater its capacity. Smaller particles will therefore generally offer higher capacity than a similar mass of larger particles, smaller crystals will generally offer higher capacity than a similar mass of larger crystals, and it will be generally advantageous to use particles or crystals of the smallest available size.

In certain embodiments, the invention provides methods for use of supersaturated or immobilized ureides to bind virus and/or endotoxin while not substantially binding proteins. The term supersaturated refers to the situation in which a particulate, powdered, or crystalline material is present at a concentration such that when the maximum amount of the material is dissolved, a solid mass remains present.

In certain embodiments, the invention provides methods for purification of virus through removal of protein. In other embodiments, the invention provides methods of purifying proteins while removing virus and endotoxin. In yet other embodiments, the invention provides methods for binding virus in connection with removing and optionally inactivating virus from a sample or local environment such as in the context of filtering virus from gas or liquid or for cleaning or protective applications.

In certain embodiments, the invention provides methods for purification of cellular organelles through removal of proteins and other small molecule contaminants. A subset of the organelles co-precipitate with supersaturating amounts of a ureide on a solid surface such as allantoin, such as in an amount ranging from 1 to 20% of the volume of the preparation in which the organelles reside. Proteins and small molecule contaminants substantially unbound to the allantoin are eliminated when the solid material is washed with a buffer containing a saturated solution of allantoin. The organelles are subsequently recovered by solubilizing the allantoin, through addition of a buffer lacking allantoin. The purified organelles can be concentrated by ultrafiltration. It will be apparent to the person of skill in the art that recovery of biologically active organelles may rely on the buffers containing soluble constituents in order to conserve biological activity or at least avoiding inclusion of conditions and compounds that may reduce biological activity.

In certain embodiments, the invention provides methods for purification of inclusion bodies through removal of contaminating proteins and other small molecules.

In certain embodiments, the invention provides methods for virus purification through use of ureide co-precipitating agents wherein virus is co-precipitated by insoluble ureide, separating the solid material with the bound desired virus, and then recovering from the solids the virus by introducing a competing agent that dissociate the virus from the ureide. This approach can benefit from the use of low solubility ureides, including allantoin and uric acid. In certain embodiments, it is advantageous to use low solubility ureides because it limits the amount of residual ureide in the resuspended virus.

In certain embodiments, the invention provides methods for virus purification through use of ureide co-precipitating agents wherein virus is co-precipitated with insoluble ureide, separating the solid material with the bound desired virus, and then recovering from the solids the virus by dissolving the ureide, for example by adding water or an appropriate non-ureide-containing buffer. Effectiveness of virus co-precipitation and recovery can be influenced by the pH and salt concentration of the environment, as well as by the relative amount of the ureide employed. In direct contrast to co-precipitation with multivalent ions, increasing the salt concentration may increase the effectiveness of ureide co-precipitation. In further contrast to co-precipitation with multivalent ions, especially the more commonly used multivalent cations, ureide precipitation may be more effective at acidic pH, even with co-precipitating virus species that exhibit strong binding to anion exchangers.

In certain embodiments directed to virus recovery, residual ureide in virus recovered by either approach is easily removed by a variety of methods, for example by ultrafiltration, coincident with virus concentration. Alternatively or additionally, especially if a higher degree of purification is desired, and since ureides are inert to most chromatography methods, they can be removed by nearly any chromatography method. Since ureides are mostly nonionic, the sample can be applied to an ion exchanger, with the result that the residual ureide is unbound and washed away while the virus is bound and subsequently eluted in a ureide free salt-containing buffer. Or, the sample can be applied to a size exclusion chromatography column, on which the virus elutes early due to its large size, well separated from the ureide which elutes very late because of its small size. Or salts can be added to the sample to cause the virus to bind to a hydrophobic interaction chromatography column, while the ureides flow through and are thus eliminated. A person of ordinary skill will recognize that other chromatography methods, or precipitation methods can be used to remove the residual ureide in conjunction with increasing the purity of the virus. This highlights the point that ureide co-precipitation may be combined with other virus purification methods, if desired, to achieve the level of purity required to meet the needs for a particular application. Soluble ureides may alternatively be removed by a membrane filtration process using a membrane with pore sizes that allow the passage of the soluble ureide but retain the biological target of interest. This approach has the additional benefit of concentrating the biological target.

In certain embodiments directed to protein or plasmid purification, the invention provides methods for the co-precipitation of virus and endotoxin with super-saturated ureides because virus and endotoxin bind to the insoluble ureide. The soluble protein or DNA plasmid may then be recovered in the supernatant by removing the insoluble co-precipitate by filtration or centrifugation. The insoluble co-precipitate may be optionally sterilized and discarded. Some care should be taken with this approach since while DNA generally appears to have a low affinity for ureides such as allantoin, DNA that is strongly associated with contaminants can be removed by the interaction of the contaminants with the ureide. Contaminant-associated DNA includes, for example, DNA associated with histones, nucleosomes, other proteins or other heterogeneous assemblages.

The invention provides in certain embodiments, methods for selectively separating virus from a sample containing virus or suspected of containing virus including the steps of (i) providing a solid having ureide moieties at its surface; (ii) contacting the sample with the solid, whereby a substantial fraction of the virus in the sample binds to the ureides on the surface of the solid; and (iii) separating the solid from the liquid fraction of the sample.

In certain embodiments, at least 50%, 70%, 80%, 90%, 95% or substantially all of the virus in the sample binds to the ureides on the surface of the solid.

In certain embodiments, the method is for the purification of a desired virus and the sample contains the desired virus.

In certain embodiments, the ureide is a supersaturated ureide such as allantoin or uric acid. In certain such embodiments, the ureide is allantoin at a concentration greater than 0.56%, 1%, 2%, 5%, 10%, 20% or more.

In certain embodiments, the liquid fraction of the sample is removed by sedimentation or filtration of the solids. In certain embodiments, the solid separated from the liquid fraction is washed by resuspension buffer saturated or nearly-saturated with allantoin to dilute contaminants in the fluid remaining in the interstices of the precipitate, and the solid is then separated from the liquid fraction. In certain embodiments, the solid separated from the liquid fraction is contacted with a resuspension buffer in an amount sufficient to solubilize the ureide. The buffer may be of various pH or salt concentration, where such conditions will generally be chosen to favor the stability of the virus, and not to substantially affect the solubility of the ureide.

In certain embodiments, the sample contains a desired biological product, the virus is a contaminant, and the method is a method for purification of the biological product. In certain such embodiments, the desired biological product is a protein, DNA plasmid, or antibody. In certain embodiments, the solid is a solid material having a plurality of ureide moieties on the surface of such solid material. In certain embodiments, the solid ureide is the insoluble portion of a supersaturated ureide such as allantoin or uric acid. In certain such embodiments, the ureide is allantoin at a concentration greater than 0.56%, 1%, 2%, 5%, 10%, or 20%, or more. In certain other embodiments the ureide is uric acid at a concentration greater than 0.0025%, 0.01%, 0.1%, 1%, 2%, 5%, 10% or more. In certain embodiments, the ureide is at a concentration greater than about two times saturation, or greater than about 1%, or greater than about 2%, or greater than about 3%, or greater than about 5%, or greater than about 10%.

In certain embodiments, the sample contains an additional contaminant selected from the group consisting of cells, cell substructures, cell fragments, aggregates, and endotoxins, and the amount of an additional contaminant is reduced by co-precipitation with the solid.

In certain embodiments, the sample is contacted with the solid for at least about fifteen minutes prior to the step of separating the solid from the liquid fraction. In certain other embodiments, the sample is incubated with the solid for less than 15 minutes or from about 15-30 minutes, or more than 30 minutes or about 60 minutes or more than about 60 minutes. As a general matter, the binding of most large biological targets with allantoin appears to be essentially instantaneous, and achieves completion in less time than a removal step can be conducted. Prudent laboratory practice nevertheless recommends that incubation time be evaluated systematically, and even if it turns out not to have a substantial effect for a particular application, a consistent treatment time should be specified and adhered to for a particular application.

In certain embodiments, while the solid contacts the sample, the sample has a pH value of less than about 4.0, or greater than about 4.0 and less than about 7.0, or greater than about 7.0 and less than about 9.0. In certain embodiments, the solid may be applied at a conductivity less than about 1 mS/cm, or greater than about 1 mS/cm and less than about 10 mS/cm, or greater than about 10 mS/cm and less than about 25 mS/cm, or greater than about 25 mS/cm and less than about 40 mS/cm, or greater than about 40 mS/cm and less than about 100 mS/cm, or more than about 100 mS/cm.

In certain embodiments, the biological target-bearing liquid may be separated from insoluble materials by sedimentation or filtration.

In certain embodiments, the invention provides methods for use of chemically modified surfaces having virus-binding capacity in order to recover virus from local environments such as in connection with filtration of virus from air or liquid. Local environments from which virus may be removed include gases, liquids, and solid surfaces. Such environments can be delivered to, contacted with, or flowed past materials of the invention for the purpose of virus removal or "filtration" from such local environments.

Ureides represent a class of organic molecules that embody at least one ureide residue. Examples include but are not limited to urea, hydantoin, allantoin, uric acid, imidazolidinyl urea (1,1'-methylenebis(3-[1-(hydroxymethyl)-2,5-dioxoimidazolidin-4-yl]urea), diazolydinyl urea (1,3-bis(hydroxymethyl)-1-(1,3,4-tris(hydroxymethyl)-2,5-dioxoimidazolidin-4-yl)urea) purines, as well as derivatives and compound constructs containing these structures. Ureides with sufficiently low solubility for convenient practice of the invention particularly include allantoin and uric acid. Highly soluble ureides may in some cases weaken the interaction of ureides on a solid surface with a large target biological entity.

In certain such embodiments, the surface of the solid additionally has a plurality of secondary chemical functionalities where the secondary chemical functionalities are selected from the group consisting of an electropositive moiety, a hydrophobic moiety, and a metal chelating moiety.

In one or more of the preceding embodiments, a sample may be conditioned for subsequent purification steps by combining one or more species of soluble organic multivalent ions with the ureide.

In one or more of the preceding embodiments, the soluble multivalent ions may be electropositive. In one such embodiment, the soluble electropositive multivalent ion may include one or more from the group consisting of (i) ethacridine, (ii) chlorhexidine, (iii) methylene blue, (iv) benzalkonium chloride, (v) polyethyleneimine, or (vi) other electropositive multivalent organic ion. In one such embodiment, the concentration of the electropositive organic multivalent ion may range between 0.001 and 0.1%.

In one or more of the preceding embodiments, the soluble organic multivalent ion may be electronegative. In one such embodiment, the soluble multivalent ion may include one or more from the group consisting of capric acid, caprylic acid or octanoic acid; in a concentration range from 0.01 to 5.0%.

In one or more of the preceding embodiments, a sample containing a ureide and one or more species of soluble organic multivalent ions may be further conditioned by (i) removing solids from the sample, (ii) providing a first component which is a first solid substrate having an electronegative surface; (iii) providing a second component which is a second solid substrate having an electropositive surface; (iv) contacting the protein preparation with the first and second components, wherein the first and second components are configured such that the sample may contact both components simultaneously, wherein the operating conditions substantially prevent the binding of the desired protein to the first or second components; and (v) separating the desired biological target from the first and second components. In one such embodiment, the sample conditions prevent substantial binding of the biological target of interest to soluble or immobilized ions. In one such embodiment, substantially preventing the binding of the biological target of interest to the multivalent ions consists of adjusting the salt concentration, or adjusting the pH, or adding an organic modifier to effectively block substantial binding of the biological target to multivalent ions.

In one or more of the preceding embodiments, a sample containing a ureide and one or more species of soluble organic multivalent ions may be further conditioned by (i) removing solids from the sample, (ii) contacting the sample with at least one solid surface comprising at least one surface-bound ligand capable of binding a metal, wherein the surface-bound ligand capable of binding a metal is initially substantially devoid of a metal, wherein operating conditions are selected to substantially prevent the binding of the desired protein to the at least one solid surface and (iii) separating the sample from the at least one surface-bound ligand; wherein when more than one surface-bound ligand is present, each surface-bound ligand is independently either of the same charge or charge neutral. In one such embodiment, the sample conditions prevent substantial binding of the biological target of interest to soluble or immobilized ions. In one such embodiment, substantially preventing the binding of the biological target of interest to the multivalent ions consists of adjusting the salt concentration, or adjusting the pH, or adding an organic modifier to effectively block substantial binding of the biological target to multivalent ions.

In one or more of the preceding embodiments, conditioning of the protein preparation comprises any combination of the aforementioned conditioning procedures or portions thereof.

In one or more of the preceding embodiments, conditioning of the sample comprises treating the protein preparation with one or more soluble organic multivalent ions having the same net charge type and at an aggregate concentration in a range of from about 0.001% to about 0.1% weight by volume, under conditions whereby the desired protein is substantially unbound to and substantially unprecipitated by the one or more soluble multivalent organic ions.

In one or more of the preceding embodiments, conditioning of the sample comprises treating the sample with one or more immobilized organic multivalent ions of the same or different net charge under conditions whereby the desired protein is substantially unbound to the immobilized organic multivalent ions.

In one or more of the preceding embodiments, at least one species of soluble or immobilized organic multivalent cation comprises a metal affinity functionality.

In one or more of the preceding embodiments, binding and precipitation of the desired protein to the one or more soluble organic multivalent ions is prevented by increasing the conductivity, altering the pH, adding blocking organic additives, or combinations thereof.

Definitions

Terms are defined so that the invention may be understood more readily. Additional definitions are set forth throughout the detailed description.

"Endotoxin" refers to a toxic heat-stable lipopolysaccharide substance present in the outer membrane of gram-negative bacteria that is released from the cell upon lysis. Endotoxins are generally acidic due to their high content of phosphate and carboxyl residues, and highly hydrophobic due to the fatty acid content of the lipid-A region. The molecular weight of individual endotoxin molecules may be as little as 10,000 D or less but they occur in this form generally in the presence of strong detergents and the absence of metal ions. In biological solutions, they typically exist as large aggregates in various physical conformations with molecular weights up to greater than 10,000,000 D. Some such aggregates are known to have a physical size of 1000 nm (1 micron) or more, and may be configured as micelles, ribbons, sheets, and complex assemblages with metal ions and other sample components that endow them with an extended size.

"Polynucleotide" refers to a biopolymer composed of multiple nucleotide monomers covalently bonded in a chain. DNA (deoxyribonucleic acid) and RNA (ribonucleic acid) are examples of polynucleotides. "DNA plasmid" refers to a closed-loop, double stranded unit of DNA with the ability to replicate within a cell independently of chromosomal DNA.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Supersaturated ureide" refers to a suspension containing an amount of ureide in excess of its maximum solubility under the conditions prevailing in a particular preparation. In certain embodiments, the invention provides a sample with a ureide present in an amount greater than such ureide's solubility in such sample under the conditions for such sample such that some fraction of such ureide is present in an undissolved form in the sample.

"Ureide" refers to a cyclic or acyclic organic molecule of natural or synthetic origin that comprises one or more ureide moieties or derivatives thereof. In certain embodiments, the invention provides ureides such as urea, uric acid, hydantoin, allantoin (CAS number 97-59-6; alcloxa, aldioxa, hemocane, ureidohydantoin, 5-ureidohydantoin, glyoxylureide, glyoxylic acid diureide, 2,5-dioxo-4-imidazolidinyl urea), imidazolidinyl urea (1,1'-methylenebis(3-[1-(hydroxymethyl)-2,5-dioxoimidazolidin-4-yl]urea), diazolydinyl urea (1,3-bis(hydroxymethyl)-1-(1,3,4-tris(hydroxymethyl)-2,5-dioxoimidazolidin-4-yl)urea), purines, and derivatives thereof. In certain embodiments, the invention provides organic molecules of the formula R—CO—NH—CO—NH2 or RCO—NH—CO—NH—CO—R' or R'R"NH—CO—NR'"R"" where the relevant "R-groups" may be H or any organic moiety.

"Virus" or "virion" refers to an ultramicroscopic (roughly 20 to 300 nm in diameter), metabolically inert, infectious agent that replicates within the cells of living hosts, mainly bacteria, plants, and animals: composed of an RNA or DNA core, a protein coat, and, in more complex types, a surrounding envelope. Examples include but are not limited to a dsDNA virus, a ssDNA virus, a dsRNA virus, a (+)ssRNA virus, a (−)ssRNA virus, a ssRNA RT virus and a dsDNA-RT virus; an adenovirus, a herpesvirus, a poxvirus, a parvovirus, a reovirus, a norovirus, a picornavirus, a togavirus, an orthomyxovirus, a rhabdovirus, a retrovirus, a hepadanvirus, a papillomavirus, a Human Immunodeficiency Virus (HIV), an influenza virus, dengue virus, Japanese encephalitis virus, West Nile virus, and bacteriophages. The term virus is understood to include virus particles for use as vectors for gene therapy, for use as vaccines, and as replacements for antibiotics. It is also understood to include so-called pseudovirions, which may be described as virus particles that have been recombinantly modified to conserve their ability to generate protective immunity while eliminating their ability to cause infection.

"Organic multivalent ion" refers to an organic molecule, ion or salt of natural or synthetic origin that embodies at least one charge and at least one additional chemical functionality, thus rendering it multivalent. In certain embodiments, an organic multivalent ion, the at least one additional chemical functionality is an additional charge such that the organic multivalent ion bears two or more like or differing charges. The organic multivalent ion may bear a net positive, net negative, or net neutral charge. Where the organic multivalent ion is net positive it may be provided together with anions such as chlorides, bromides, sulfates, organic acids, lactates, gluconates, and any other anion not incompatible with the method. In certain embodiments certain of the positive charges of the organic multivalent ion are supplied by amine, imine or other nitrogen moieties. The organic multivalent ion may additionally be of mixed chemical character and include hydrophobic residues, other functional moieties and/or it may possess the ability to participate in other types of chemical interactions including, for example, the ability to participate in hydrogen bonds, hydrophobic interactions, pi-pi bonding, metal coordination, and intercalation. Examples of positively charged organic multivalent ions in certain embodiments include but are not limited to the diamino acids, di-, tri, or larger homo- or hetero-peptides, such as polylysine, polyarginine, polyhistidine, polyornithine; polyethyleneimine; polyallylamine; polydimethrine, polymethylacrylamidopropyltrimethylammonia; polydiallyldimethylammonia; polyvinylbenzyltrimethylammonia; polyvinylguanidine; poly(N-ethyl-4-vinylpyridine; DEAE-dextran; DEAE-cellulose; ethacridine (CAS number 442-16-0; 7-ethoxyacridine-3,9-diamine); tris (2-aminoethyl)amine; guanidine; chlorhexidine; alexidine; citricidal, protamine; spermine; spermidine; salmine; chitosan; and variants and derivatives of the foregoing. For example, variants and derivatives of ethacridine are understood to include 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), and salts thereof (e.g. chlorides, bromides, sulfates, lactates, gluconates.) Where the organic multivalent ion is net negative it may be provided together with cations such as sodium or potassium, or any other cation not incompatible with the method. In certain embodiments certain of the negative charges of the organic multivalent ion are supplied by carboxyl, phospho, or sulfo moieties. The organic multivalent ion may additionally be of mixed chemical character and include hydrophobic residues, or other functional moieties and/or it may possess the ability to participate in other types of chemical interactions including, for example, the ability to participate in hydrogen bonds, hydrophobic interactions, pi-pi bonding, metal coordination, and intercalation. Examples of negatively charged organic multivalent ions in certain embodiments include but are not limited to fatty acids such as capric acid, caprylic or octanoic acid, anionic polymers, and salts thereof (e.g. chlorides, bromides, sulfates, lactates, gluconates).

In certain embodiments, the invention provides methods in which ureide co-precipitation occurs by chemical affinity of virus particles for super-saturated ureides. Smaller contaminants such as proteins, nucleotides, salts, sugars, and other small-molecule sample components are not co-precipitated, and thus remain soluble in the liquid. Virus product can then be recovered, if desired, by adding sufficient water or an appropriate non-ureide-containing buffer to resolubilize the supersaturated ureide while the virus can also spontaneously regain solubility as the ureide dissolves. Alternatively, the solid can be discarded, leaving the liquid with a reduced amount of virus.

In certain embodiments of the invention which rely upon co-precipitation of supersaturated ureide and a virus, a ureide species that embodies low to moderate solubility may be used. Highly soluble ureides may disadvantageously require the use of excessively high total amounts of ureide whereas near-insoluble ureides require excessive volumes of water to solubilize the supersaturated ureide to which the virus is bound. Allantoin is an example of a ureide with suitable solubility characteristics. It saturates at concentration of about 36 mM, corresponding to a weight-to-volume (w/v) proportion of 0.56%. As a general matter, effectiveness may increase at higher ureide proportions, such as 1-5%, or up to 10%, or more.

Urea and hydantoin are examples of ureides with inconveniently high solubilities. Hydantoin is roughly 10 times more soluble than allantoin, and urea about 100 times more soluble. Uric acid is an example of a ureide with excessively low solubility, saturating at about 0.0025% w/v, meaning that solubilization of a single gram would require nearly 40 L of water.

In certain embodiments where the objective is to recover a desired large biological target from the solid, the development of a method customized to provide the best results for a particular application begins with selection of the ureide. In certain embodiments, the water-resolubilization format will be simplest to develop and operate, and generally offer the best recovery. Allantoin is well suited to this format. An amount of 5-10% is a convenient place to start. Other ureides may be evaluated, but experimental data to date indicate that allantoin is consistently the most effective candidate.

In certain embodiments, co-precipitation of virus with ureides may be influenced by the pH and salt concentration of the environment. In one embodiment, the treatment occurs at a pH value ranging from pH 3 to 9, and a conductivity of less than 1 to more than 50 mS. Experimental data indicate that variations with respect to pH and conductivity derive mainly from variations in the inherent solubility of the virus, and not with the affinity of allantoin for the virus. With pH and conductivity specifications defined, it may be advantageous in certain embodiments to determine the amount of ureide required to fully precipitate the virus. This is easily determined by experiments at different increments of ureide. It will rarely be necessary to employ more than 10%, although it may be possible.

If the aqueous-resolubilization format is selected for separation of the virus from the ureide, it is advantageous in certain embodiments to determine the pH and conductivity conditions for the resuspension buffer that support the most effective virus precipitation. This can be done with simple experiments conducted over a range of pH and conductivity values. The experimental workload can be reduced with statistical methods for design of experiments (DoE). Evaluate a pH range of at least 5 to 8, and conductivity values from 15 mS/cm, up to at least 50 mS/cm. These conductivity values correspond to a range of physiological conductivity to about half molar sodium chloride. Lower conductivity values may be evaluated but may impose the extra logistical burden of diluting or buffer exchanging the virus sample. As a general matter, special attention should be given to the infectivity of the recovered virus. In the event that recovery of infective virus is a particular objective of the method, buffer conditions for dissolving the allantoin should be chosen particularly to favor conservation of infectivity. Such conditions will frequently be known, independently from the invention, and may be applied without reducing the effectiveness of the invention as a whole.

In certain embodiments directed to virus purification, it may be desirable to recover virus by chemical dissociation from the solid ureide, because this will reduce the liquid volume to be processed in comparison with the approach of simply dissolving the allantoin. Such an approach may result however in lower recovery and impose a higher risk that infectivity of the recovered virus is reduced. Given the strongly polar nature of ureides, and their extensive hydrogen bonding potential, highly soluble ureides are reasonable candidates to consider, including urea, or particularly ureides with greater structural similarity to allantoin, such as imidazolydinyl urea. To the extent that infectivity is not a necessary feature of the purified virus, its loss may not be a concern. In either case, experiments will be required to determine the appropriate concentration of the dissociating agent. It will be apparent to the person of ordinary skill in the art that it is also possible to pursue a recovery strategy that involves both dissolution of allantoin and the use of a dissociating agent.

In certain embodiments directed to protein purification and/or virus removal, a convenient starting point for customizing the method to a particular application is to simply add 5% of the chosen ureide to a sample, incubate for 15 minutes or more, remove the precipitate, then evaluate the supernatant for recovery of the protein or plasmid of interest, as well as for the amount of virus and/or endotoxin content. Method conditions may be further evaluated with a subsequent series of experiments in which one may vary the amount of ureide, pH, and conductivity. The total number of experiments may be reduced by applying statistical methods for design of experiments. Experimental data indicate that binding kinetics are so rapid as to make long incubation unnecessary. Results from incubations longer than 15 minutes do not indicate significant improvement in removal of virus or endotoxin. This parameter can be easily evaluated nevertheless to ensure that an adequate binding interval is documented for a particular application. In those embodiments where the objective is to enhance the effectiveness of both virus removal and also virus inactivation at low pH, evaluation of suitable conditions may advantageously be focused upon the identity of the target and amount of the ureide, applied at the previously established low pH conditions.

In certain embodiments directed to protein or plasmid purification and virus removal, the invention provides the advantage that residual ureides appear to be inert to most chromatography surfaces and can therefore be easily removed by binding the protein or plasmid of interest to a chromatography support, and allowing the ureide to flow through. It is within the purview of a person of ordinary skill to select a method appropriate to the particular protein or plasmid. One general example, pertinent to purification of IgG, would be to apply the invention following elution of the IgG from a column of protein A, add allantoin under conditions suitable for virus inactivation by low pH, incubate, remove the insoluble allantoin, then adjust the sample conditions and apply the sample to a cation exchange column, thereby binding the IgG. Wash with equilibration buffer to remove trace levels of allantoin, then elute the IgG as usual. Another general example, pertinent to purification of a DNA plasmid, would be to bind the plasmid to an anion exchange or hydroxyapatite column. Wash away the excess ureide, then elute with NaCl or phosphate, respectively, to obtain the ureide-free plasmid.

In certain embodiments directed to protein or plasmid purification, the method can be applied in conjunction with virus inactivation at low pH to achieve more effective virus reduction than either method alone. Ureide co-precipitation may be combined with other protein or plasmid purification methods as desired to achieve the level of purity required to meet the needs for a particular application. Soluble allantoin and uric acid are substantially inert to most chromatography surfaces, which means that they can be eliminated easily by binding the protein of interest to a chromatography support, and allowing the ureide to flow through the column. Experimental data indicate that more than 99% of soluble residual ureide is reduced in a first chromatography step, such as a cation exchange chromatography step or an affinity chromatography step, and that ureide content is reduced below the level of detectability after a second chromatography step, such as an anion exchange or hydroxyapatite chromatography step.

In certain embodiments, virus products captured on supersaturated ureides can be processed in the same fashion, or by a mechanism that is unique in the field of precipitation-based methods. For example, virus is bound to supersaturated allantoin, protein contaminants are removed with the supernatant, then the virus recovered by solubilizing the allantoin through simple addition of water, thereby releasing the virus. Now-soluble allantoin can then be removed by simple ultrafiltration, or other means.

Certain embodiments of the invention provide the advantage that a precipitation method can be based on supersaturated levels of a precipitating agent, but not on soluble levels of such agents. For example, soluble allantoin has no practical effect on virus solubility whereas supersaturated allantoin co-precipitates virus. Thus, subsequent solubilization of previously supersaturated allantoin with bound virus by simple addition of water releases the virus from the newly solubilized allantoin. Experimental data indicates that the ability of ureides, including allantoin, to bind virus but not protein, reflects a size-component to its selectivity. This indicates in turn that ureide-modified surfaces offer parallel capability to scavenge other classes of microbes, and potentially inactivate at least some of those classes. Such classes may include bacteria, mycoplasma, and protozoans.

In certain embodiments, the apparent ability of supersaturated allantoin to selectively bind large biological targets such as virus can be used to enhance the deliberate suspension of biological function of the virus, for example where the objective is to inactivate the virus so that it loses its ability to infect its normal host. Such applications include the inactivation of virus by treatment at low pH where allantoin is included, or inactivation of virus by treatment with organic multivalent cations such as ethacridine, methylene blue, benzalkonium chloride, chlorhexidine, or organic multivalent anions such as caprylic acid, or by non-ionic organic solvents such as tri(n-butyl)phosphate potentially in combination with a non-ionic surfactant, or by a surfactant independent of tri(n-butyl)phosphate, or combinations of the foregoing. The apparent ability of allantoin to bind by hydrogen bonding means that it does not interfere with, and is not itself interfered with by these inactivating treatments. In addition to and independent of the specific inactivation method, the ability of supersaturated allantoin to bind virus, and thereby physically remove it from a sample, is understood to directly contribute to the overall reduction of infective virus from a given sample.

In certain embodiments, insoluble ureides bound to surfaces can bind endotoxin, but curiously exhibit little ability to bind DNA. This extends the potential utility of such embodiments to remove both endotoxin and/or virus from protein preparations and/or preparations containing DNA plasmids. In other embodiments where the DNA exists in stable complexes with other sample components, allantoin has the effect of removing the DNA by virtue of removing the complexes with which the DNA is associated.

In some embodiments, there are provides kits for the convenient practice of any of the methods disclosed herein. Such kits may include the reagents and a set of general instructions for carrying out the methods. In addition to kits, those skilled in the art will recognize that the methods disclosed herein may be formatted for use in various applications such as in anti-viral and/or anti-microbial respiratory filters, masks, systems for the emergency detoxification of water, and the like.

It is to be understood that both the foregoing general description and the following detailed description are exemplary and explanatory only and are not restrictive of the invention, as claimed.

EXAMPLES

The following examples illustrate methods by which aspects of the invention may be practiced or materials suitable for practice of certain embodiments of the invention may be prepared.

Example 1

Purification of the Virus, Bacteriophage M13 by Coprecipitation with Allantoin Phage cell culture supernatant was co-precipitated by addition of allantoin at a weight to volume ratio of 7%. pH was about 7.0. Conductivity was 20 mS. The virus was recovered by dissolving the allantoin in 50 mM Hepes, 150 mM NaCl, pH 7.0. Phage recovery was about 70%. Greater than 99% of proteins and small molecule contaminants were eliminated with the supernatant.

Example 2

Co-Precipitation of Bacteriophage M13

Example 1 was repeated at pH values of 5.0, 6.0, and 8.0% allantoin. Co-precipitation efficiency over the range of both examples, as judged by removal from the supernatant, was inversely correlated with pH.

Example 3

Co-Precipitation of Bacteriophage M13

Example 1 was repeated at NaCl concentrations corresponding to conductivity values of 40, 60, 80, and 100 mS/cm. These salt concentrations correspond with about 400, 600, 800, and 1000 mM NaCl. Precipitation efficiency, as judged by removal of virus from the sample, was directly correlated with conductivity. Optimal co-precipitation occurred at 400 mM NaCl. This was interpreted to reflect suppression of mutual electrostatic repulsion among viral particles with the result of supporting higher packing density of the particles on the ureide surface.

Example 4

Co-Precipitation of Bacteriophage M13

Example 1 was repeated with 3%, 5%, and 10% allantoin. Co-precipitation efficiency, as judged by removal from supernatant, was directly correlated with allantoin concentration. Recovery increased from about 31% to 57% to 91% respectively.

Example 5

Co-Precipitation of Bacteriophage M13

Phage cell culture supernatant was precipitated with 7% allantoin at 400 mM NaCl, pH 6.0. The majority of proteins and small molecule contaminants were eliminated with the supernatant. Recovery was estimated to be in excess of 90%. The virus was recovered by dissolving the allantoin in 50 mM Hepes, pH 7.0, then concentrated by ultrafiltration. Purity from the combined process were estimated by analytical anion exchange chromatography to be in excess of 90%; recovery about 80%.

Example 6

Co-Precipitation of Attenuated Dengue Virus

Attenuated Dengue virus was combined with 7% allantoin at 600 mM NaCl, pH 6.0. The supernatant was removed. The virus was recovered by dissolving the allantoin in 50 mM Hepes, pH 7.0. Recovery was estimated by immunoassay to be 70-80%. Host protein contamination was reduced by 99.3%.

Example 7

A viral culture containing $10^{10}$ particles per mL of minute virus of mice was coprecipitated under physiological conditions by addition of allantoin in an amount of 10%. Infectivity testing of the supernatant documented removal of 99.9% of the virus.

Example 8

A viral culture containing $10^{10}$ particles per mL of murine leukemia virus was coprecipitated under physiological conditions by addition of allantoin in an amount of 10%. Infectivity testing of the supernatant documented removal of 99.9% of the virus.

Example 9

Virus Removal from a Protein Preparation by Co-Precipitation with Allantoin Phage M13 cell culture supernatant was co-precipitated by addition of allantoin at a weight to volume ratio of 5%. pH was about 7.0. Conductivity was about 15 mS. About 60% of the virus was eliminated in the precipitate. The majority of proteins remained in the supernatant.

Example 10

Endotoxin Reduction from a Protein Solution

A sample of ovalbumin in 50 mM phosphate, 100 mM NaCl, pH 7.2, contaminated with about 50 EU/mL of endotoxin, was saturated with 3% allantoin, incubated for 15 minutes, following which the precipitate was removed by membrane filtration. Endotoxin content of the supernatant was reduced by more than 95%, to less than 2 EU per mL. The experiment was repeated with 10% allantoin. Endotoxin was reduced by more than 99.5%, to less than 1 EU/mL.

Example 11

Recovery of Antibody and Endotoxin Reduction from an IgG-Endotoxin Mixture Using Ureides on a Solid Surface Endotoxin was added to 1 mg/mL human IgG in 5 mM HEPES 100 mM NaCl pH 7.0 to 22,000 EU/ml. 2% (w/v) allantoin were added to aliquots of this mixture and allowed to mix for 15 minutes at room temperature. The suspension was clarified by centrifugation. Protein and endotoxin concentrations were measured to calculate antibody recovery and endotoxin removal. 2% (w/v) allantoin reduced endotoxin twofold. Antibody recovery was unaffected by the amount of allantoin. In a subsequent series of experiments, the amount of allantoin was increased in increments, up to 10%. Antibody recovery diminished gradually to about 93% at 10% allantoin, while endotoxin removal efficiency increased to about 99%. These experiments illustrate that the use of excessive amounts of allantoin can result in a loss of some proteins. In such cases, the person of skill in the art can make an informed decision as to the most productive balance of endotoxin removal versus protein recovery, and adjust the availability of the solid phase ureide accordingly. Additional experiments with proteins ranging in size from about 12 kDa to 1 MDa indicated a definite trend whereby the loss of protein increases with increasing protein size.

Example 12

Comparison of Allantoin and Uric Acid as Substrates for Removal of Endotoxin Endotoxin was added to a 6.7 mg/mL solution of human IgG in 5 mM Hepes, 100 mM NaCl, pH 7.0 to a final concentration of 13,000 EU/ml. 1, 2 and 4% (w/v) of either allantoin or uric acid was added to aliquots of this mixture and allowed to mix for 15 minutes at room temperature. As a control, equal amounts of potato starch were added to a separate series. Finally, the reaction mixtures were clarified by centrifugation. Protein and endotoxin concentrations were measured to calculate antibody recovery and endotoxin removal. There was no reduction in endotoxin with the addition of starch. Uric acid produced a 4-fold reduction at all concentrations. Allantoin reduced endotoxin from 5-10-fold across the experiments (low to high). Antibody recovery was greater than 90% throughout. Besides the poorer performance of uric acid, the fact that results were unchanged as a function of the amount of uric acid are puzzling, and highlight allantoin as being a preferable ureide to begin with.

Example 13

Accelerated Clarification of Mammalian Cell Harvest by Addition of Allantoin

Allantoin was added to a final concentration of 1% to 5 L of cell-containing cell culture harvest containing an IgM monoclonal antibody, among the usual spectrum of contaminants. The container was swirled gently to mix the components. Interactions between allantoin and unknown cell culture components caused this amount of allantoin to be fully soluble, so an additional 1% was added, bringing the total added amount to 2% (w/v). The container was again swirled to mix the components. Whereas particulate materials had been observed to settle very slowly before addition of allantoin, and only slightly faster in the presence of 1% allantoin, settling rate was obviously accelerated by 2% allantoin, and left the cell culture supernatant sparkling optically clear. The differential between 1% and 2% allantoin was interpreted as an indication that 1% allantoin, by virtue of the presence of some solubilizing substances in the sample, was almost completely solubilized by the sample. The supernatant was subsequently decanted. This inadvertently resuspended a portion of the precipitate, which was subsequently centrifuged to sediment the remaining solids. Beyond its virus and endotoxin removal capabilities, this highlights the ability of the invention to improve the quality of cell harvest clarification. It also highlights the practicality of conducting initial trials with an allantoin concentration of at least 2%. It further highlights the important point that the solubility of allantoin may be affected by components of a sample, with the effect that a supersaturating concentration of allantoin will ultimately be determined experimentally, although its known solubility in water may provide a useful preliminary guide.

Example 14

Clarification of an *Escherichia coli* Lysate by Addition of Allantoin 20 grams of *E. Coli* paste in 250 mL of 50 mM Hepes, pH 7.0 past was homogenized with a microfluidizer at 16,000× g. The homogenate was then centrifuged at 15,000×g for 1 hour to remove the largest particulate species. This produced a tan-colored turbid supernatant. Dry allantoin was added directly to the supernatant to a final concentration of 5% w/v. The mixture was swirled for about 1 minute than allowed to settle. Insoluble materials settled within a few minutes leaving an optically sparking clear supernatant that contained more than 90% of the protein product that was present in the original homogenate. The supernatant passed easily through a 0.22 micron membrane filter, where supernatant prior to allantoin treatment clogged the filter virtually on contact. This example highlights the ability of allantoin to dramatically improve the filterability of a treated sample.

Example 15

Effect of Organic Additives at the Allantoin Affinity Step

Cell-containing mammalian cell culture harvest containing a monoclonal IgG was treated by allantoin affinity with 1% allantoin in combination with 0.01% ethacridine. The sample, at a pH of about 7.2 and a conductivity of about 13.5 mS, these conditions corresponding with so-called physiological conditions, was passed over a column packed chromatography media including equal amounts of the metal affinity ligand TREN (BioWorks TREN hi-sub) and a hydrophobic ligands (Macroprep T-butyl). Antibody recovery following the previous steps was 99%. DNA was reduced by 3.5 logs, and virus was reduced by 4-5 logs. In addition, the treated sample was sparking clear, with a turbidity of about 2.0 NTU, indicating near-total removal of particulates.

Example 16

The form or example 15 was followed except increasing the amount of allantoin over the course of a series of experiments, including 2%, 4%, and 8%. Antibody recovery decreased in a roughly linear fashion in inverse proportion to the amount of allantoin. Whereas recovery at 1% (example 15) was 99%, recovery at 8% was about 87%.

Example 17

IgG processed as described in examples 15 and 16 was analyzed by size exclusion chromatography. Results showed a roughly linear decrease in aggregate content with increasing allantoin, but the decrease in aggregate content was greater than the loss of antibody noted in example 16. Where aggregate content following example 15 was about 5%, it was reduced to about 1.3% at 8% allantoin. Aggregate content of membrane clarified cell harvest lacking allantoin was about 19%. It was also observed that increasing amounts of allantoin preferentially reduced the higher molecular weight aggregates. This example highlights the functional feature of the invention that supersaturated allantoin preferentially binds biological targets of higher molecular weight. It also highlights the important developmental perspective that the actual amount of allantoin used to process a particular biological target can be adjusted to favor aggregate removal, or antibody recovery.

Example 18

Allantoin and ethacridine were added to 5% serum-supplemented monoclonal IgM supernatant, to final concentrations of 1% (super-saturation) and 0.02% respectively. The supernatant was clarified by centrifugation and then flowed through a packed chromatography bed (20 mL supernatant per mL packed bed) comprising a combination of microporous and macroporous electropositive and electronegative media, plus microporous lipophilic particles in equal volumes: QAE Sephadex A-25, SP Sephadex C-25, Nuvia Q, Nuvia S and Sephadex LH-20. The IgM was then captured over a cation exchanger. IgM recovery was 80% over the two-step process and the purity was more than 90% by analytical SEC, with no apparent aggregates.

Example 19

One liter of monoclonal IgG-containing cell culture supernatant was treated with 1% allantoin and 0.02% ethacridine for 15 minutes. The yellow precipitate was removed by membrane filtration, and the optically sparkling clear bright yellow filtrate was applied to 10 mL column filled with an equal mixture of Chelex 100 and Macroprep High Q. The treated material was then applied to a protein A column to a load of 20 mg/mL, washed for 10 column volumes, and the IgG eluted. Comparison of the eluted IgG with antibody eluted from protein A loaded with untreated cell culture supernatant contained roughly 80 times lower host cell protein contaminants, 10 ppm versus 800 ppm. These results particularly highlight the ability of the invention to remove contaminants that are not effectively removed by downstream purification methods. Parallel experiments were set up to determine the dynamic binding capacity of protein A columns loaded with treated and non-treated samples. Dynamic capacity on the column loaded with treated sample was about 20% higher than the column loaded with untreated sample, 35 mg/mL versus 28 mg/mL. These results particularly highlight the ability of the invention to remove contaminants that interfere directly with the function of downstream purification methods.

Example 20

Figure 1:
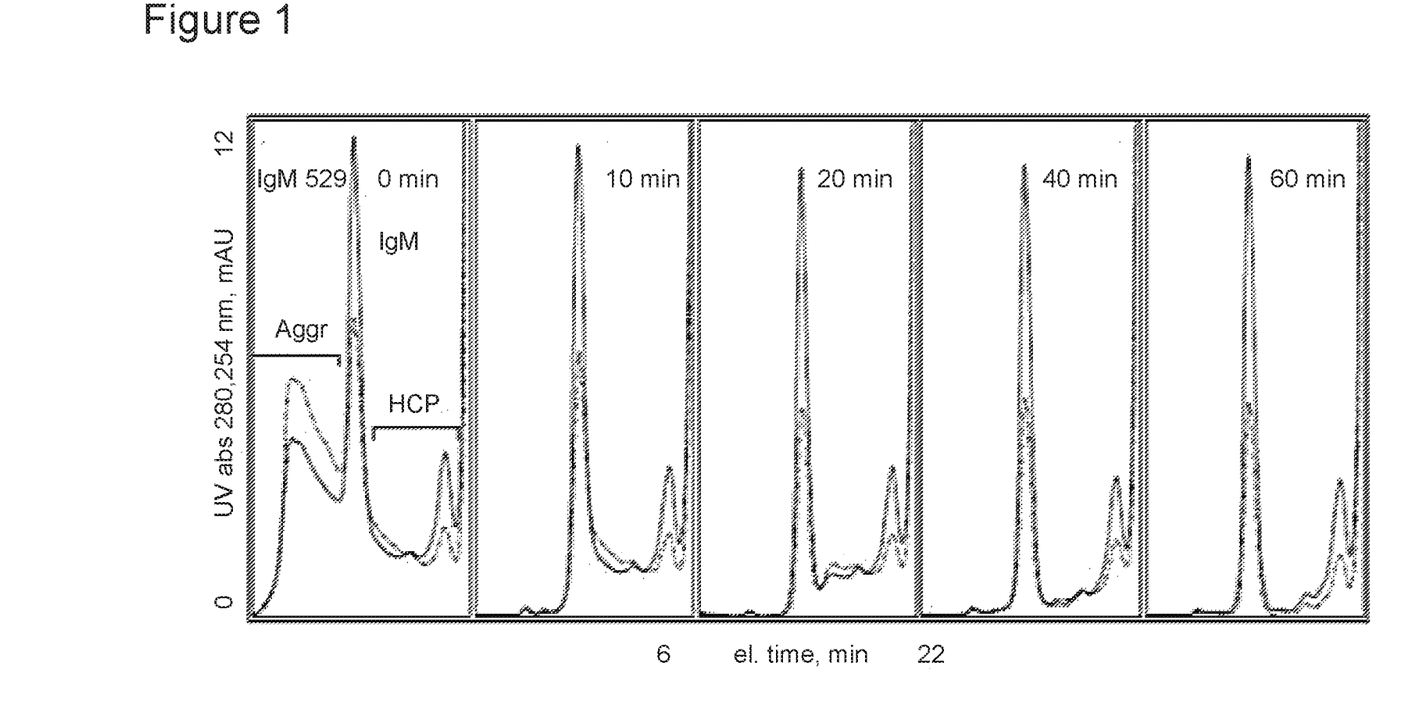
Figure 1 shows a time course plot indicating a reduction in high molecular weight aggregates and reduction of host cell protein contaminants in accordance with methods disclosed herein.

An equal mixture of negatively charged metal-chelating styrene divinylbenzene particles (Chelex 100), positively charged polymethacrylate porous particles Macroprep High-Q, and negatively charged polymethacrylate particles (MacroPrep High-S) was mixed with a sample of IgM-529 that had been previously treated with NaCl to a final conductivity of 20 mS/cm, 1% allantoin, and 0.025% ethacridine. The volumetric ratio of particles to sample was 1:20. Samples were taken at 10 minutes, 20 minutes, 40 minutes, and 60 minutes, and the particles were removed by microfiltration. Figure 1 shows a dramatic reduction of high molecular weight aggregates at all time points, but with progressively greater reduction of all aggregates over time, accompanied by a substantial apparent reduction of host cell protein contaminants as well. Subsequent analysis showed that the reduction of both aggregates and host proteins reflected the combined reduction of chromatin remnants from the sample. Ethacridine was also removed from the samples at all time points.

Example 21

Figure 2A:
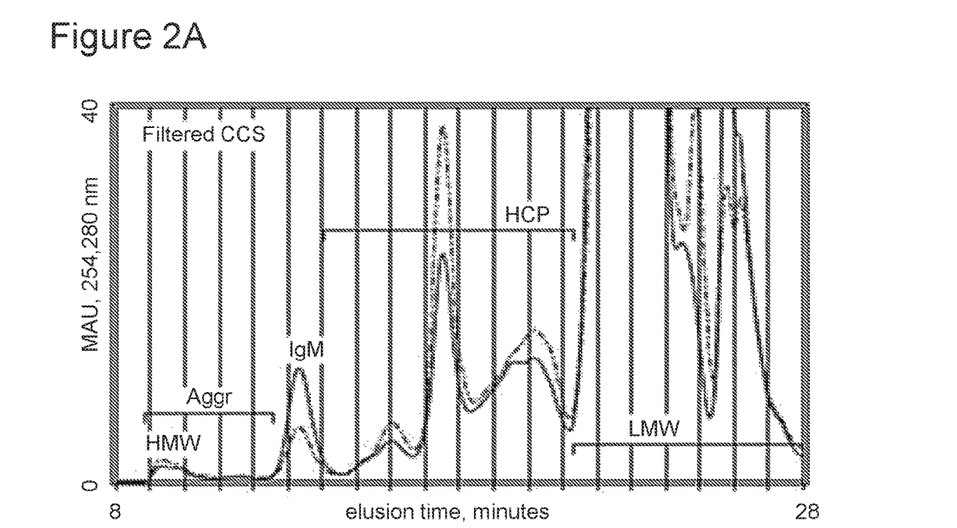
Figures 2A and 2B show size exclusion chromatography profiles before and after treatment of IgM-84 antibody in accordance with methods disclosed herein.
Figure 2B:
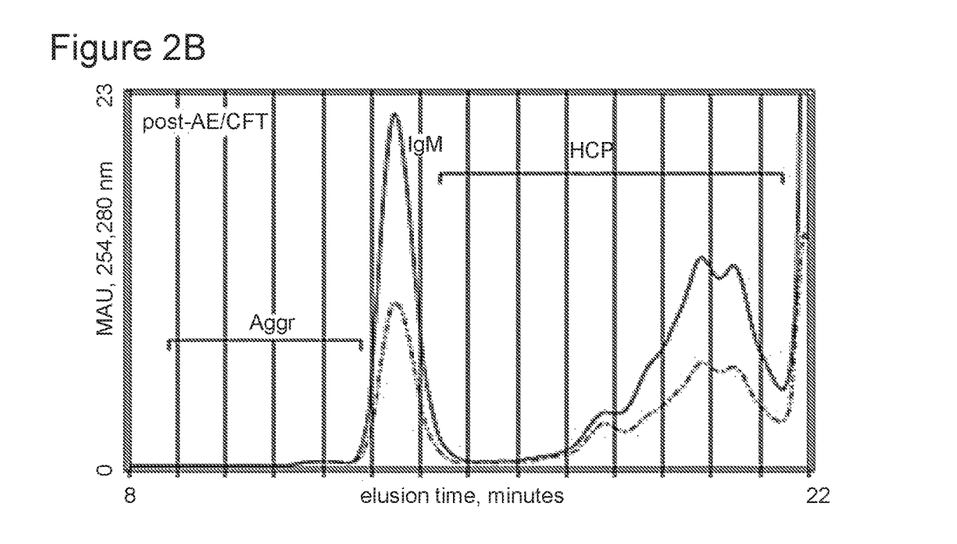

Figures 2A and 2B illustrate size exclusion chromatography profiles before and after treatment of IgM-84 treated with 200 mM NaCl, 1% allantoin, and 0.025% ethacridine, and then treated with the same media mixture as in Example 7, but by passing the sample though a device in which the mixed media were sandwiched between woven polymer retainers of adequately narrow mesh to retain the particles. HMW aggregate was completely eliminated, along with the majority of smaller aggregates. Table 1 below shows that DNA and histones were initially distributed across all aggregate fractions, with the IgG fraction, and across all protein-containing fractions.

TABLE 1

IgM and contaminant content of SEC fractions.

| EIT, min | [IgM] | DNA size | [DNA] | [His] | 254:280 |
|---|---|---|---|---|---|
| 9 | 0.31 | bld | 10 | 0.13 | 1.31 |
| 10 | 0.09 | bld | 10 | 0.11 | 1.30 |
| 11 | 0.42 | bld | 10 | 0.13 | 1.03 |
| 12 | 0.68 | (150-1000) | 12 | 0.13 | 0.98 |
| 13 | 20.29 | bld | 44 | 0.21 | 0.49 |
| 14 | 21.08 | (660) | 236 | 0.76 | 0.89 |
| 15 | 2.33 | 445/(660) | 459 | 1.87 | 0.97 |
| 16 | 0.30 | 316/445 | 435 | 0.82 | 1.59 |
| 17 | 0.51 | 316 | 796 | 1.09 | 1.45 |
| 18 | 0.38 | 155/316 | 314 | 0.96 | 1.60 |
| 19 | 0.31 | 90/155 | 339 | 0.33 | 1.40 |
| 20 | 0.09 | 90 | 684 | 0.86 | 1.56 |
| 21 | bld | 58 | 123 | 1.33 | 0.90 |
| 22 | bld | bld | 23 | 0.54 | 1.21 |
| 23 | bld | bld | 13 | bld | 3.67 |
| 24 | bld | bld | 3 | bld | 15.86 |

EIT: elution time, minutes.
[IgM]: concentration in micrograms/mL.
DNA size in base pairs (bp). Values in parentheses from DNA detected in ion exchange experiments.
[DNA] concentration in ng/mL.
[HIS]: total histone concentration, micrograms/mL.
bld: below limit of detection.

Table 1 also illustrates the size distribution of DNA, which led to the unexpected discovery that some aggregate populations included nucleosomal arrays containing various numbers of nucleosomes, in addition to DNA and histones. Recovery of IgM from this treatment was 98%.

Example 22

Figure 3:
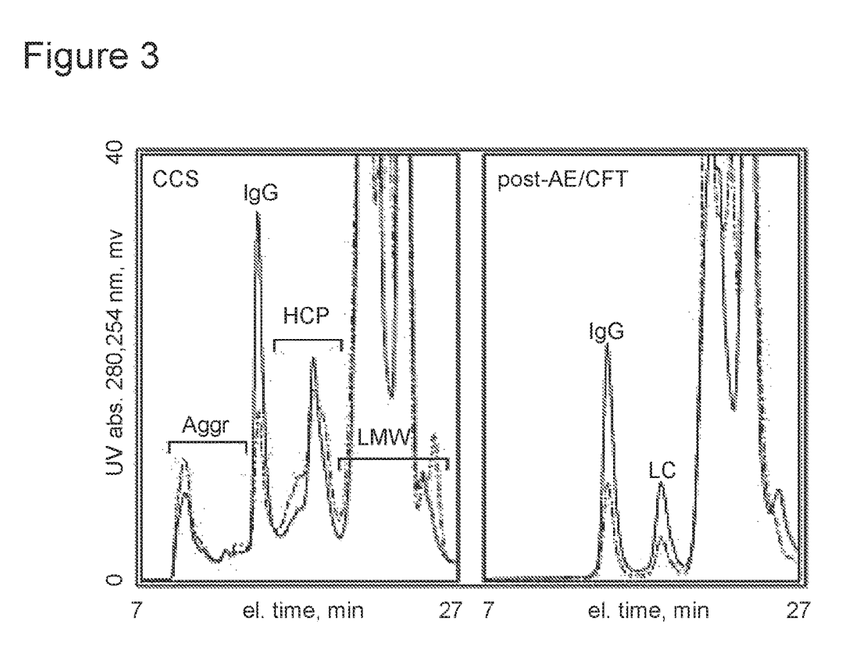
Figure 3 shows size exclusion chromatography profiles before and after the treatment of an anti-HER2 monoclonal IgG antibody in accordance with methods disclosed herein.

Figure 3 illustrates size exclusion chromatography profiles before and after the same procedure of Example 19 of an anti-HER2 monoclonal IgG antibody. The results are the same in kind, but improved in degree, likely, at least in part, because the concentration of the antibody is about 10 times higher.

Example 23

1 L of cell culture harvest was treated by addition of 1% allantoin and 0.025% ethacridine and incubated stirring for 15 minutes, after which the cells and other particulates were removed by centrifugation. The supernatant was passed through an assembly containing equal proportions of styrene divinylbenzene particles substituted with iminodiacetic acid, agarose particles substituted with TREN, and acrylate particles substituted with butyl residues, with a combined volume of 50 mL, dimensions of 2.6×10 cm, and a flow rate of 25 mL/min. Initial aggregate content of greater than 12% was reduced to less than 0.1%. Excess ethacridine was removed. Host protein contamination was reduced 60%. DNA, as measured by qPCR was reduced by 6 logs. Antibody recovery was 99%.

Example 24

1 L of cell culture harvest was treated by addition of 1% allantoin and 0.025% ethacridine and incubated stirring for 15 minutes, after which the cells and other particulates were removed by centrifugation. The supernatant was passed through an assembly containing equal proportions of styrene divinylbenzene particles substituted with iminodiacetic acid, styrene divinylbenzene particles substituted with amino groups, and acrylate particles substituted with butyl residues, with a combined volume of 50 mL, dimensions of 2.6×10 cm, and a flow rate of 25 mL/min. Initial aggregate content of greater than 12% was reduced to less than 0.1%. Antibody recovery was 95%. Results were otherwise identical to example 20.

Example 25

A 1 mg/mL preparation of purified DNA from salmon sperm was treated with 5% allantoin. More than 95% of the DNA remained soluble in the supernatant. This highlights the utility of separating virus or endotoxin contaminants from DNA preparations, such as plasmid preparations, which is otherwise extremely difficult because all three bind strongly to electropositive surfaces such as anion exchangers. These results were unexpected however because results from many previous examples showed that DNA levels were reduced by 98 to 99% or more in antibody-containing protein preparations. The apparent discrepancy appears to be resolved by allantoin having little or no inherent affinity for DNA, but a very high affinity for DNA associated with other molecule, especially including DNA-compaction proteins or other compound associations of DNA with chromosomal substructures particularly including nucleosomes and their prokaryotic analogues. This further highlights the point that applications to purification of polynucleotides will likely benefit in particular from being conducted at high salt concentrations and/or the presence of organic modulators that discourage nonspecific formation of polynucleotide complexes with contaminants.

Example 26

Enhancement of Virus Inactivation at Low pH

A cell culture supernatant containing about $10^{10}$ particles of murine leukemia virus per mL was split into 10 aliquots. Half of the aliquots were treated by reduction of pH to 4 for the purpose of inactivating the virus. The other half was treated by the same reduction or pH plus the addition of 10% allantoin. Aliquots representing treatment at 1, 5, 10, 15, and 60 minutes were evaluated for virus infectivity. At 1 minute, inactivation absent allantoin was 1.2 logs versus 2.4 logs with allantoin. At 5 minutes, inactivation absent allantoin was 3.2 logs versus 4.5 logs with allantoin. At 10 minutes, inactivation absent allantoin was 4.3 logs versus 5.4 logs with allantoin. At 15 minutes, inactivation absent allantoin was 5.1 logs versus 5.6 logs with allantoin. At 60 minutes, inactivation absent allantoin was 5.4 logs versus 5.6 logs with allantoin. Since the sensitivity of the infectivity assay is about 5.5 logs, it is likely that the allantoin inclusion increases the level of inactivation at all time points, in addition to accelerating inactivation. It will be apparent to the person of skill in the art that combination of allantoin with other virus inactivation methods will likely have a similar enhancing effect.

Example 27

Enhanced Clarification of a Monoclonal IgG-Containing Cell Culture Supernatant by Combination of Supersaturated Allantoin with an Organic Multivalent Anion Cell-containing harvest was clarified by centrifugation and membrane filtration through a 0.22 micron membrane, then the pH of the supernatant was reduced to 6.0. Various subsamples were treated with octanoic acid at amounts of 0.01%, 0.05%, and 0.1%. All samples were turbid following treatment, indicating the persistence or reformation of particulates, even after precipitated materials were removed by centrifugation. The same series of experiments was repeated in the presence of 2% allantoin. Antibody recovery and reduction of contaminants was essentially equivalent but the processed material was sparkling clear after processing.

Example 28

Endotoxin Removal During Purification of a DNA Plasmid

Powdered allantoin was added to a final concentration of 10% in a filtered *E. coli* lysate containing a DNA plasmid. The mixture was stirred for 15 minutes then the solid allantoin was removed by microfiltration. 96.7% of the endotoxin was removed with the allantoin. 80% of the DNA plasmid was recovered in the filtrate. This example illustrates the relatively high affinity of allantoin for endotoxin and low affinity for DNA, and reveals allantoin to be an important tool for removing endotoxin from DNA plasmid preparations, such as those containing DNA plasmids as gene therapy vectors. From the results given in the previous Examples, it will be apparent to the person of ordinary skill, that in the case of plasmids produced in mammalian cells, allantoin treatment will offer the additional benefit of virus removal.

It will be understood by the person of ordinary skill in the art how to scale up the results from experiments such as those described in the above examples, to whatever volume required to meet their particular requirements.

The present invention may be combined with other purification methods to achieve higher levels of purification. Examples include, but are not limited to affinity chromatography, anion exchange chromatography, cation exchange chromatography, hydrophobic interaction chromatography, immobilized metal affinity chromatography, and additional mixed mode chromatography methods. It is within the purview of a person of ordinary skill in the art to develop appropriate conditions for the various methods and integrate them with the invention herein to achieve the desired purification of a particular antibody, protein, virus, phage, plasmid or other biological product as desired. Additionally, the methods of the invention may be exploited or adapted for use in conjunction with the purification of biological products, diagnostic and/or therapeutic medical devices, and devices for personal or public protection from virus infection.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present invention.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

The invention claimed is:

1. A method of selectively separating a biological target from a sample comprising the biological target or suspected of comprising the biological target, the method comprising: (i) contacting the sample with a supersaturated allantoin, wherein at least 50% of the biological target in the sample binds to the supersaturated allantoin, thereby forming an undissolved precipitate comprising allantoin and the biological target; and (ii) separating the undissolved precipitate from the sample.

2. The method of claim 1, wherein the biological target has a size in a range from about 10 nm to about 200 nm.

3. The method of claim 1, wherein the biological target is a large biological target having a molecular weight in a range of about 10 megaDaltons or greater.

4. The method of claim 1 wherein the biological target comprises a cell.

5. The method of claim 4, wherein the cell is a mammalian cell.

6. The method of claim 1, wherein the biological target comprises a substructure of a cell.

7. The method of claim 6, wherein the cellular substructure comprises an organelle.

8. The method of claim 6, wherein the cellular substructure comprises an exosome.

9. The method of claim 1, wherein at least 75% of the biological target binds to the supersaturated allantoin.

10. The method of claim 1, wherein at least 90% of the biological target binds to the supersaturated allantoin.

11. The method of claim 1, wherein at least 95% of the biological target binds to the supersaturated allantoin.

12. The method of claim 1, wherein at least 99% of the biological target binds to the supersaturated allantoin.

13. The method of claim 1, wherein substantially all of the biological target binds to the supersaturated allantoin.

14. The method of claim 1, wherein the supersaturated allantoin comprises crystalline allantoin.

15. The method of claim 1, wherein the supersaturated allantoin is in an aqueous liquid and comprises undissolved allantoin in the form of a solid by virtue of allantoin being present in the aqueous liquid at a supersaturating concentration.

16. The method of claim 1, wherein the supersaturated allantoin is at a concentration greater than 0.56%.

17. The method of claim 1, wherein the undissolved precipitate is separated from the sample by filtration or sedimentation.

18. The method of claim 17, wherein, after (ii), the undissolved precipitate is washed by re-suspending the undissolved precipitate in a clean buffer then recovering the undissolved precipitate by sedimentation or filtration.

19. The method of claim 18, wherein the clean buffer comprises allantoin at or close to saturation.

20. The method of claim 18, wherein the washing step may be repeated one or more times.

21. The method of claim 19, wherein the biological target is separated from at least some of the allantoin in the recovered undissolved precipitate by solubilizing the at least some of the allantoin.

22. The method of claim 21, wherein the biological target is subsequently concentrated by diafiltration.

23. The method of claim 21, wherein the solubilizing is performed simultaneous with concentrating the biological target by diafiltration.

24. The method of claim 22, wherein the biological target is subsequently purified by an additional fractionation method.

25. The method of claim 1, wherein the sample is a liquid or a gas.

26. The method of claim 1, wherein the sample is a cell culture harvest containing cells or lysed cells.

27. The method of claim 26, wherein the cells may have been previously removed.

28. The method of claim 1, wherein the sample is aqueous.

29. The method of claim 1, wherein the sample is water.

30. The method of claim 1, wherein the sample is air.

31. The method of claim 1, wherein the biological target is a desired biological target to be purified.

32. The method of claim 1, wherein the biological target is a biological target to be removed from the sample.

33. The method of claim 32, wherein the biological target may comprise more than one species of biological target to be removed from the sample.

34. The method of claim 32, wherein the sample is treated with one or more species of soluble organic multivalent ions with the same net charge at an aggregate concentration ranging from 0.001 to 0.1%.

35. The method of claim 34, wherein the one or more species of soluble organic multivalent ions comprises one or more species from the group of ethacridine, chlorhexidine, or octanoic acid at a concentration ranging from 0.001 to 0.1%.

36. The method of claim 32, wherein the sample is treated with one or more species of immobilized organic multivalent ions of the same or different net charge, on a solid surface under conditions where the biological target does not bind to the immobilized organic multivalent ions.

37. The method of claim 32, wherein the sample is treated with both soluble and immobilized organic multivalent ions, and wherein at least one species of immobilized organic multivalent ions has a net charge opposite to the soluble organic multivalent ions.

38. The method of claim 37, wherein the immobilized organic multivalent ions include species of opposite net charge.

39. The method of claim 34, wherein the one or more species of soluble organic multivalent ions comprises a metal affinity functionality.

40. The method of claim 37, wherein treatment with the soluble organic multivalent ions occurs prior to treatment with the immobilized organic multivalent ions, or treatment with the soluble organic multivalent ions and treatment with the immobilized organic multivalent ions occurs essentially at the same time.

41. The method of claim 1, wherein the method is practiced at a pH value of 4-10.

42. The method of claim 1, wherein the method is practiced at a conductivity of 1-100 mS cm.

43. The method of claim 1, wherein the sample is incubated together with the supersaturated allantoin for a period of time of 60 minutes.

44. The method of claim 1, wherein the biological target is a virus being subjected to a treatment to inactivate the virus.

45. The method of claim 44, wherein the virus inactivating treatment comprises exposure to a pH of 3 to 5.

46. The method of claim 1 wherein the biological target has a molecular weight of about 1 megaDalton to about 10 megaDaltons.

47. The method of claim 1 wherein the biological target is a protein.

48. The method of claim 1, wherein the biological target is endotoxin.

49. The method of claim 1 wherein the biological target is a virus.

* * * * *